United States Patent
Shockley

(10) Patent No.: US 9,265,908 B2
(45) Date of Patent: Feb. 23, 2016

(54) INTUBATING STYLETTE DEVICE AND RELATED METHODS

(71) Applicant: Airway Management Enterprises LLC, Wellesley, MA (US)

(72) Inventor: Richard Shockley, Wellesley, MA (US)

(73) Assignee: Richard Shockley, Wellesley, MA (US)

( * ) Notice: Subject to any disclaimer, the term of this patent is extended or adjusted under 35 U.S.C. 154(b) by 399 days.

(21) Appl. No.: 13/759,342

(22) Filed: Feb. 5, 2013

(65) Prior Publication Data

US 2013/0199522 A1 Aug. 8, 2013

Related U.S. Application Data

(60) Provisional application No. 61/633,188, filed on Feb. 8, 2012.

(51) Int. Cl.
*A61M 16/04* (2006.01)

(52) U.S. Cl.
CPC ........... *A61M 16/0488* (2013.01); *A61M 16/04* (2013.01)

(58) Field of Classification Search
CPC .. A61B 1/00045; A61B 1/005; A61B 1/0056; A61B 1/0057; A61B 1/0669; A61B 1/122; A61B 1/126; A61B 1/267; A61B 1/2676; A61B 17/28; A61B 17/2909; A61B 19/34; A61B 5/14539; A61B 5/1459; A61M 1/00; A61M 1/008; A61M 16/00; A61M 16/04; A61M 16/0418; A61M 16/0463; A61M 16/0472; A61M 16/0488; A61M 16/06; A61M 25/01; A61M 25/0102; A61M 25/0136; A61M 25/0138; A61M 25/0144; A61M 25/0147; A61M 25/0152; A61M 25/09; A61M 25/09025; A61M 25/09033; A61M 25/09041; A61N 1/00; A61N 1/05; A61N 1/056; A61N 1/365; B08B 9/04
USPC ............. 128/200.26, 207.14, 207.15, 207.16, 128/207.18, 912; 600/104, 120, 131, 144, 600/146, 156, 184, 323, 434, 585; 604/119, 604/174, 264, 267, 523, 524, 528, 902, 604/95.01, 95.04
See application file for complete search history.

(56) References Cited

U.S. PATENT DOCUMENTS

| | | | | |
|---|---|---|---|---|
| 3,521,620 | A * | 7/1970 | Cook | 600/585 |
| 4,976,688 | A * | 12/1990 | Rosenblum | 604/95.04 |
| 5,195,968 | A * | 3/1993 | Lundquist et al. | 604/95.04 |
| 5,791,338 | A * | 8/1998 | Merchant et al. | 128/200.26 |
| 6,033,378 | A * | 3/2000 | Lundquist et al. | 604/95.01 |
| 6,629,924 | B2 | 10/2003 | Aydelotte | |
| 2010/0318031 | A1 | 12/2010 | Henry | |
| 2012/0204866 | A1 | 8/2012 | Kizer | |
| 2013/0006083 | A1 | 1/2013 | Langer | |
| 2013/0014750 | A1 | 1/2013 | Etesham | |

\* cited by examiner

*Primary Examiner* — Annette Dixon
(74) *Attorney, Agent, or Firm* — Hoffman Warnick LLC

(57) ABSTRACT

Various embodiments of the invention include an intubating stylette device and related methods of using such a device. In some cases, the stylette includes: a handle member having a base and a tip extending from the base, the handle for engaging a hand of an operator; a control member coupled to the tip of the handle member, the control member including at least one actuation member sized to engage with a finger from the hand of the operator; and a tube member coupled to the control member, the tube member including a tip that is movable between at least two positions when the at least one actuation member is moved from a first position to a second position.

20 Claims, 7 Drawing Sheets

INTUBATING STYLETTE DEVICE AND RELATED METHODS

CROSS-REFERENCE TO RELATED APPLICATION

This application claims priority to U.S. provisional patent application No. 61/633,188, filed on Feb. 8, 2012, which is hereby incorporated by reference in its entirety.

TECHNICAL FIELD

Aspects of the invention relate generally to medical devices and their usage. More particularly, various aspects of the invention relate to medical devices used in conjunction with the administration of anesthesia.

BACKGROUND

Endotracheal intubation is a medical procedure in which a tube is placed through a patient's mouth and into the patient's trachea to create an artificial air passage for breathing. Typically, an endotracheal tube is used on a patient undergoing surgery to provide for the administration of anesthesia, when ventilation of the lungs is necessary, or when a patient is somehow injured and has lost the ability to breath independently (e.g., in an emergency-type setting).

As is known in the art, in the human anatomy, the epiglottis sits over the glottis opening to the larynx to prevent ingested material (e.g., food) from entering the trachea during eating. In order to insert an endotracheal tube into the trachea, the epiglottis is displaced from the glottal opening. During a conventional intubation procedure, the patient is positioned horizontally, their head is tilted back, and the mouth is opened as widely as possible. The laryngoscope is then inserted through the mouth and into the throat, and used to displace the tongue and epiglottis so that the glottis is exposed. The patient's larynx may then be seen through the mouth (or via a video display when using a video laryngoscope). The endotracheal tube is then inserted, through the mouth along the blade of the laryngoscope, and into the glottis and trachea. The endotracheal tube can accommodate a stylette, which is used to aid in inserting the endotracheal tube into the patient's trachea.

In emergency-type settings, this intubation procedure may be performed by individuals with varying levels of medical experience and skill (e.g., emergency medical technicians (EMTs), paramedics, physicians in training, emergency room physicians, etc.). Because these individuals may lack skill and experience in performing these intubation procedures, the failure rate of such procedures can be relatively high (e.g., resulting in damage to the patient's trachea or other tissue, or more serious consequences such as brain damage and death).

Further, in the non-emergency setting, such as when administering anesthesia, endotracheal intubation can be difficult when a patient's throat and/or trachea region is somehow obstructed, or the anatomic path from the mouth to the trachea is tortuous. Conventional intubation devices and techniques may cause damage to tissue within the patient's airway (throat) and/or the trachea region. Damage to the airway can lead to swelling and possibly bleeding, which makes intubation even more challenging, e.g., with multiple attempts.

BRIEF SUMMARY

Various embodiments of the invention include an intubating stylette device and related methods of using such a device. In some cases, the stylette includes: a handle member having a base and a tip extending from the base, the handle for engaging a hand of an operator; a control member coupled to the tip of the handle member, the control member including at least one actuation member sized to engage with a finger from the hand of the operator; and a tube member coupled to the control member, the tube member including a tip that is movable between at least two positions when the actuation member is moved from a first position to a second position.

A first aspect of the invention includes an intubating stylette. The intubating stylette can include: a handle member having a base and a tip extending from the base, the handle for engaging a hand of an operator; a control member coupled to the tip of the handle member, the control member including at least one actuation member sized to engage with a finger from the hand of the operator; and a tube member coupled to the control member, the tube member including a tip that is movable between at least two positions when the actuation member is moved from a first position to a second position.

A second aspect of the invention includes a method performed by an operator. The method can include inserting an intubating stylette into a throat region of a patient. In various embodiments, the method can also include inserting the intubating stylette along with an endotracheal tube telescoped on the stylette. The intubating stylette can include: a handle member with a base and a tip extending from the base, the handle for engaging a hand of the operator; a control member coupled to the tip of the handle member, the control member including at least one actuation member sized to engage with a finger from the hand of the operator; and a tube member coupled to the control member, the tube member including a tip that is movable between at least two positions when the at least one actuation member is moved from a first position to a second position. The method can further include: actuating the at least one actuation member to initiate movement of the tube member between the first position and the second position while the intubating stylette is within the throat region of the patient.

A third aspect of the invention includes an intubating stylette. The intubating stylette can include: a handle member for engaging a hand of an operator; a control member coupled to the handle member, the control member including at least one actuation member sized to engage with a finger from the hand of the operator; and a tube member coupled to the control member, the tube member including a tip that is movable across a range of positions in response to the at least one actuation member being moved across a corresponding range of positions.

Figure 1:
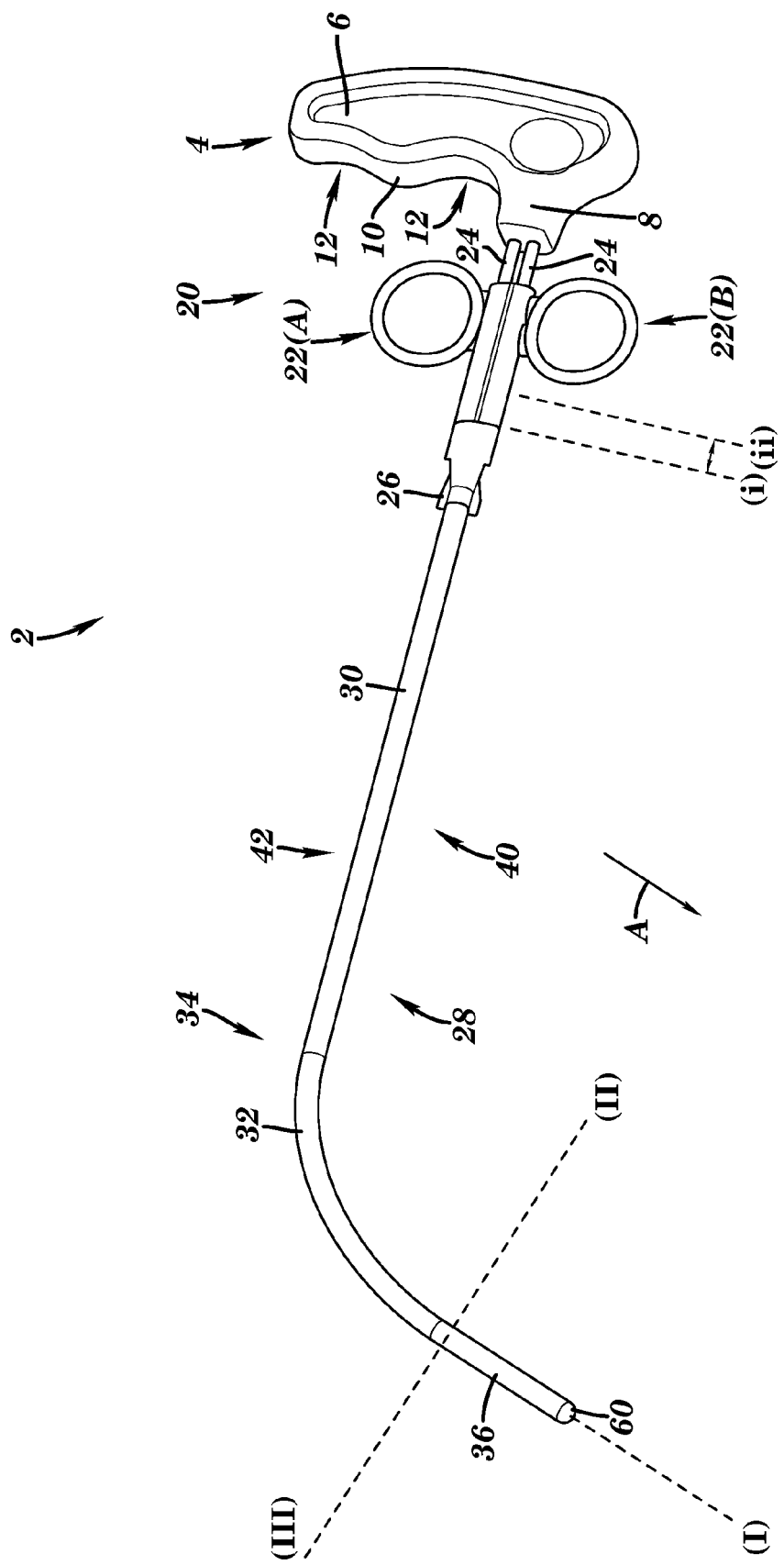
FIG. 1 shows a three-dimensional perspective view of an intubating stylette device according to various embodiments of the invention.

It is noted that the drawings of the invention are not necessarily to scale. The drawings are intended to depict only typical aspects of the invention, and therefore should not be considered as limiting the scope of the invention. In the drawings, like numbering represents like elements between the drawings.

DETAILED DESCRIPTION

As noted herein, aspects of this invention relates generally to medical devices and their usage. More particularly, various aspects of the invention relate to medical devices used in conjunction with the administration of anesthesia and/or the treatment of a medical emergency.

In the following description, reference is made to the accompanying drawings that form a part thereof, and in which is shown by way of illustration specific exemplary embodiments in which the present teachings may be practiced. These embodiments are described in sufficient detail to enable those skilled in the art to practice the present teachings and it is to be understood that other embodiments may be utilized and that changes may be made without departing from the scope of the present teachings. The following description is, therefore, merely exemplary.

As noted herein, in emergency-type settings, endotracheal intubation may be performed by individuals with varying levels of medical experience and skill, e.g., first responders. Because these individuals may lack skill and experience in performing these intubation procedures, the failure rate of such procedures can be relatively high (e.g., resulting in damage to the patient's trachea or other tissue, or more serious consequences such as brain damage and death). Further, in the non-emergency setting, such as when administering anesthesia, endotracheal intubation can be difficult when a patient's throat and/or trachea is somehow obstructed, or the path from the mouth to the trachea is tortuous. Conventional intubation devices and techniques may cause damage to tissue within the patient's airway (throat) and/or the trachea region. Damage to the airway can lead to swelling and possibly bleeding, which makes intubation even more challenging.

While some devices have been developed to enable a first responder to perform intubation procedures, the inventor has discovered that such devices suffer from several drawbacks. For example, those devices can be difficult to manipulate with a single hand because their manipulating mechanism does not interact effectively with a handle. In some cases, it may be difficult for the operator to switch between actuating the intubating device's tip in a first direction and a second direction. Additionally, the flexibility of the distal end of these devices can be insufficient to navigate a tortuous trachea passageway.

In contrast to conventional devices and approaches for endotracheal intubation, various embodiments of the invention include hand-controlled intubating stylette(s) that can be effectively manipulated using a single hand. The intubating stylette(s) disclosed herein can be effectively used, e.g., by a first responder with little intubation experience, or a skilled anesthesiologist with significant experience performing intubation procedures. In various embodiments, the intubating stylette includes at least two finger ports, e.g., for receiving and interacting with at least two of an operator's fingers, which allow the operator to alternately actuate a finger port and initiate movement of the distal end of the stylette to facilitate insertion into the trachea.

As noted herein, various embodiments of the invention include an intubating stylette and methods of using such a stylette during a medical procedure. The intubating stylette can be used in conjunction with a video laryngoscope or standard laryngoscope. As is known in the art, laryngoscopes are used to view the airway of a patient (e.g., a human patient). In particular cases, the intubating stylette is designed for use in administering anesthesia to a patient. In some other cases, the intubating stylette is designed for use in emergency medical procedures, e.g., to protect the patient's airway.

As described herein, various embodiments of the invention include an intubating stylette with a tip (tip of the tube section) that is movable between at least three positions: a) a rest position; b) an upward position, and c) a downward position opposing the upward position. The tip can be actuated using an actuation member that is proximate the stylette handle.

Various aspects of the invention allow the intubater to place the endotracheal tube into the airway during situations when conventional intubating devices have been unsuccessful. As described herein, anatomical variations may limit access to a patient's airway, making conventional intubation techniques ineffective. In some situations, video techniques involving video laryngoscopes are used to visualize the patient's airway during difficult intubation procedures. However, using a video laryngoscope requires the use of a stylette that allows the intubater to control the tip of the stylette while intubating. In contrast to conventional devices, the intubating stylette disclosed according to various embodiments of the invention gives the intubater control of the intubating tip, which can allow the intubater to quickly and effectively place the endotracheal tube into the airway.

The intubating stylette disclosed according to various embodiments includes a "pistol-like" handle with at least two finger ports (e.g., for the index and middle fingers) to control the direction of the stylette tip. The finger ports are operably connected with the flexible tip, e.g., by a wire or other substantially inelastic connector. The finger ports enable the operator to manipulate the distal tip of the stylette up to ninety degrees in one or more directions from the rest position with respect to the primary entry/exit axis (A) of the stylette. The intubating stylette can maneuver through tortuous passages within the patient's airway, allowing for use in conjunction with an endotracheal tube (e.g., an armored endotracheal tube or a standard endotracheal tube). The stylette according to various embodiments of the invention can allow for placement of an endotracheal tube over the stylette, to advance the endotracheal tube through the patient's airway. In some cases, the same operator or another operator (e.g., an assistant) can insert the endotracheal tube into the airway and advance the tube over (and past) the distal end of the intubating stylette. As noted, it is also possible that the intubater (operator) can manipulate the endotracheal tube along with the intubating stylette, e.g., one on each hand. The stylette according to various embodiments of the invention can allow at least one relatively novice operator (e.g., one not specially trained to work with intubation devices) to work with a more skilled practitioner in performing an intubation procedure. Further, the stylette can allow a solo operator (e.g., skilled practitioner or in some cases, a relative novice) to perform an intubation procedure.

Turning to FIG. 1, a three-dimensional perspective view of an intubating stylette 2 is shown according to various embodiments of the invention. As shown, the intubating stylette (or simply, stylette herein) 2 can include a handle member 4 for engaging the hand of an operator, such as a human operator. The handle member 4 can include a base 6, and a tip (handle tip, or, tip of handle 4) 8 extending from the base 6. The base 6 can include at least one contour 10 and at least one recess 12 for engaging the hand of the operator, allowing the operator to securely grip the base 6 during use of the stylette 2.

Coupled to the handle member 4 (e.g., at or proximate to the handle tip 8) is a control member 20. In some particular embodiments, the control member 20 can include at least one actuation member 22 (two shown, as 22A and 22B, respectively) sized to engage with a finger from the hand of the operator. In some cases, as shown, the control member 20 can include two substantially symmetrical actuation members 22, each sized to engage a finger from the operator's hand. In some cases, an operator can hold the handle member 4 (at its base 6) with three fingers (ring finger, pinkie finger and thumb), and engage at least one of the actuation members 22 with the index and/or middle finger. Each actuation member 22 can move along a corresponding actuation member guide 24, included in the control member 20. In some cases, the actuation member guide 24 includes a cylindrical member spanning substantially a length of the control member 20 along the primary axis (A) of the stylette 2.

The control member 20 can be coupled with a tapered retainer member 26 (optionally), which connects the control member 20 and a tube member 28. The tapered retainer member 26 can include one or more internal passageway(s) for allowing an inelastic coupler to pass between the control member 20 and the tube member 28. In various embodiments, the tapered retainer member 26 has two end openings: a first end opening 27 (FIG. 3) coupled to the control member 20; and a second end opening 29 (FIG. 3) coupled to the tube member 28. The tapered retainer member 26 can be tapered from its first end opening 27 to it second end opening 29, where the second end opening 29 is narrower than the first end opening 27.

The tube member 28 is coupled with the control member 20 via the tapered retainer member 26 in some embodiments. The tube member 28 can include: a substantially rigid substantially straight section 30 coupled to the control member 20 (via the tapered retainer member 26 in some embodiments, or directly coupled in other embodiments); a substantially rigid arced section 32 directly coupled to the rigid section 30 at a distal end 34 of the rigid substantially straight section 30; and a tip section 36 (or simply, tip) that is movable between at least two positions. It is understood that the substantially straight section 30 and the substantially rigid arced section 32 can be formed of any substantially rigid material, e.g., a metal, a composite, etc. The tip 36 can be formed of any substantially flexible material, e.g., a semi-rigid composite, deformable plastic, etc. The substantially rigid arced section 32 can be coupled with the tip 36 that is movable between at least two positions (I) and (II) (e.g., when the actuation member 22 is moved from a first position (i) to a second position (ii)). In some embodiments, the tip 36 is movable between at least three positions (I), (II) and (III). In these cases, the actuation member 22 can actuate movement of the tip 36 between these at least three positions (I), (II) and/or (III). The first position (I) can be considered a rest position (or default position), that correlates with no actuation from the actuation member(s) 22. This rest position is illustrated in FIG. 1, where actuation members 22A and 22B are in their default positions. The second position (II) can be considered a positive displacement position, which correlates with actuating actuation member 22B on the top side 40 of the stylette 2. The third position (III) can be considered a negative displacement position, which correlates with actuating actuation member 22A on the bottom side 42 of the stylette 2. The positive displacement position (II) can span between approximately one (1) degree and approximately ninety (90) degrees from the rest position (I) as measured in a first direction from axis (A), which defines the primary axis of entry of the stylette 2. The negative displacement position (III) can span between approximately one (1) degree and approximately ninety (90) degrees from the rest position (I) as measured in a second direction from axis (A). That is, the tip 36 can be movable across a range of approximately 180 degrees (+90 to −90) according to various embodiments of the invention.

As is described further herein, the stylette 2 includes a substantially inelastic connector 70 (FIG. 5, FIG. 6, FIG. 7B) that connects each of the at least one actuation member(s) 22 with the tip 36, more particularly, with the end cap 60 of the tip 36. In various embodiments, the substantially inelastic connector 70 (FIGS. 5, 6 and 7B) can include at least one wire, which is coupled with the actuation member(s) 22. While the substantially inelastic connector (or simply, connector) 70 is described as being substantially inelastic, it is understood that in some example embodiments this connector 70 can have a modulus of elasticity (tensile elasticity, or Young's modulus (E)) that is approximately greater than that of rubber, e.g., greater than approximately 0.01-0.1 gigapascals (GPa). In any cases, the substantially inelastic connector 70 has an inelastic characteristic that allows the connector 70 to respond to movement of the actuation member 22 by exerting a tensile force on the end cap 60. It is understood that the connector 70 can include a conventional wire or other substantially inelastic connector, which does not substantially deform in response to the exertion of force by the actuation member 22. It is understood that the semi-rigid tip 36 of the tube member 28, in some particular examples, can have a modulus of elasticity that allows the tip 36 to bend when the actuation member 22 is actuated, and the connector 70 is pulled into tension. As described herein, the tip 36 can be formed substantially of a material including one or more of a rubber, plastic, composite, etc. that can deform in response to movement of the connector 70. It is understood, however, that after the actuation member 22 is released, the tip 36 has a sufficiently low modulus of elasticity to return the tip 36 substantially back to its rest position (I).

Figure 2:
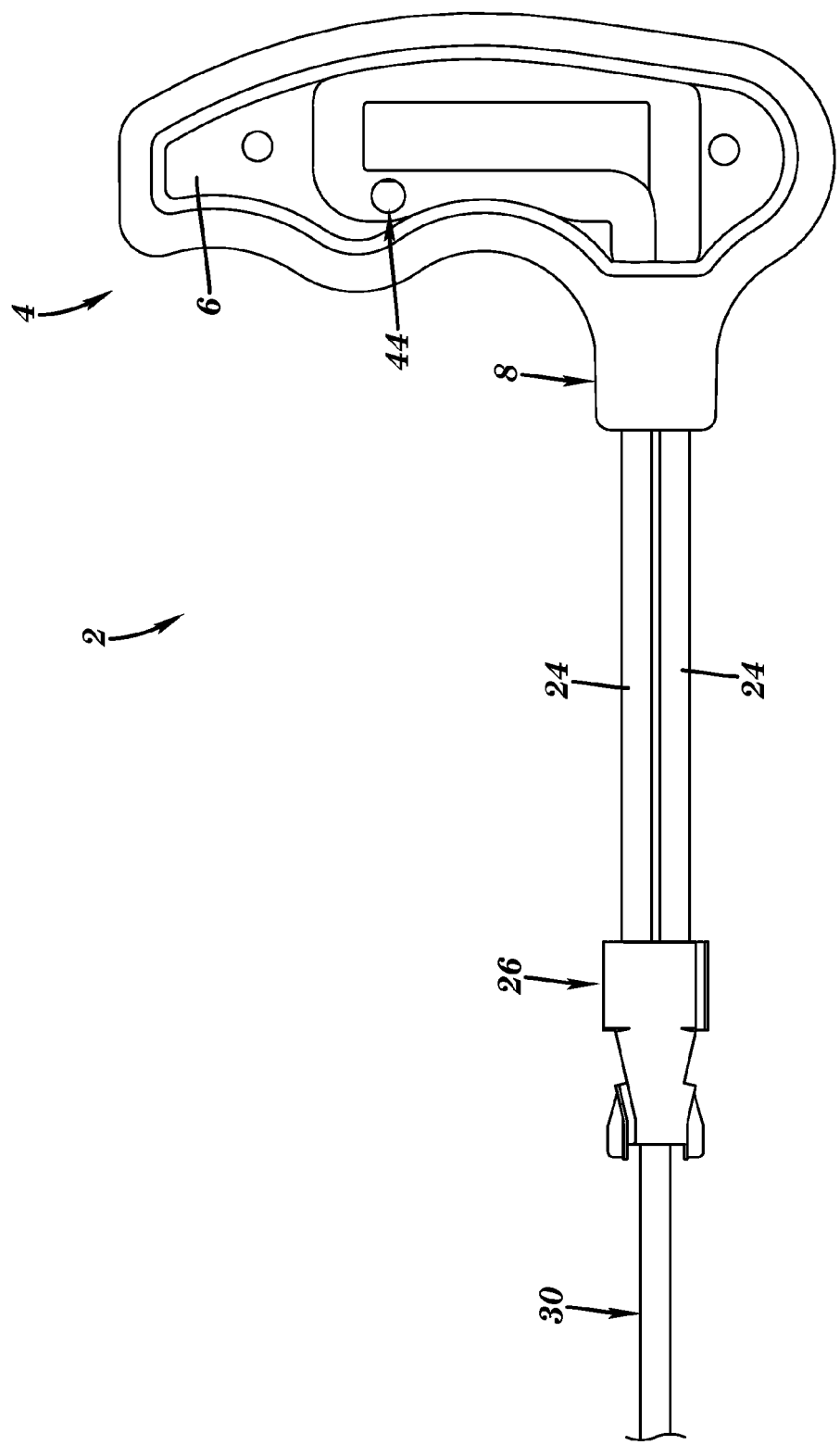
FIG. 2 shows a partial cut-away view of a section of the stylette of FIG. 1.

FIG. 2 shows a partial cut-away view of a section of the stylette 2 according to various embodiments. As shown, the stylette 2 can include a skeletal frame 44 in some embodiments that can be partially contained within the handle 4, as well as form the guide members 24. As shown, each guide member 24 can couple to the tapered retainer member 26, and define a path of movement of the at least one actuation member(s) 22 (FIG. 1).

Figure 3:
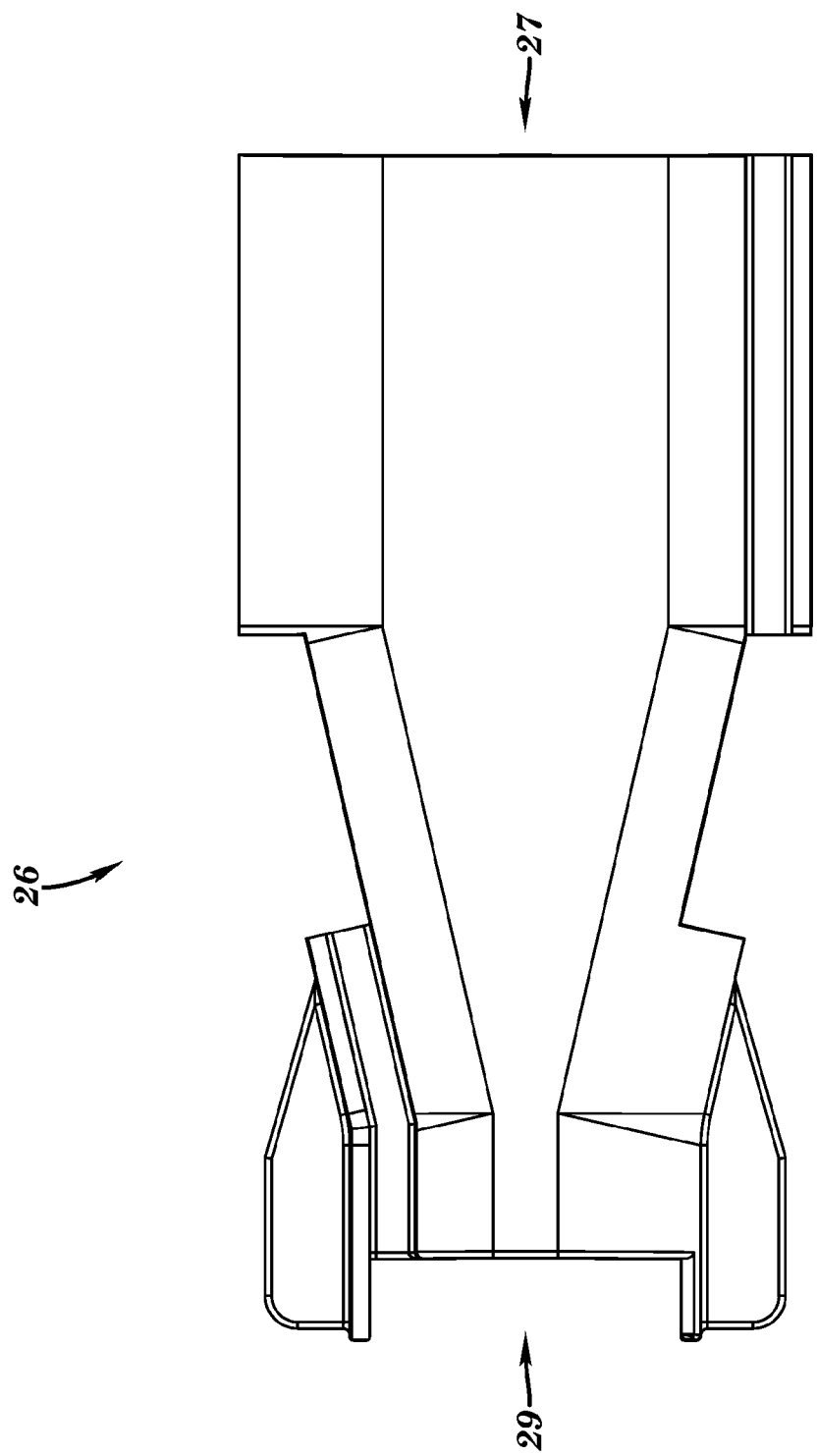
FIG. 3 shows a close-up side view of a tapered retainer member according to various embodiments of the invention.

FIG. 3 shows a close-up side view of the tapered retainer member 26, illustrating the size differential between the first end opening 27 and the second end opening 29, according to some embodiments.

Figure 4:
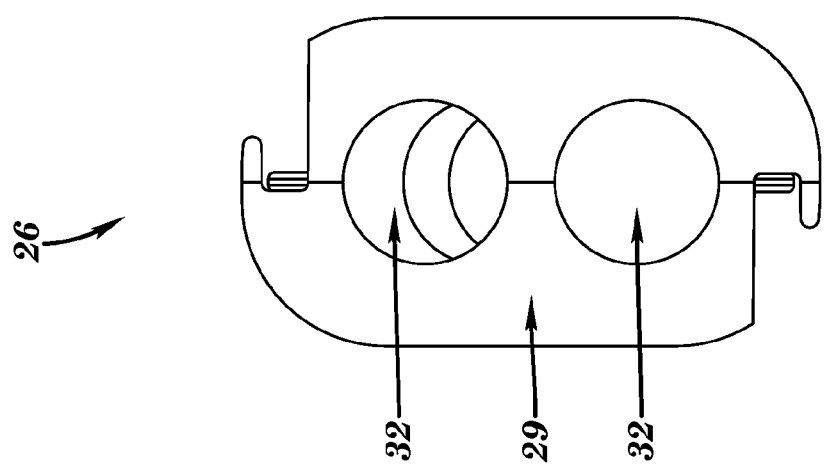
FIG. 4 shows an end view of the tapered retainer member of FIG. 3.

FIG. 4 shows an end view of the tapered retainer member 26 from the second end opening 29 (narrower end). As shown, the second end opening 29 can include two apertures 32 for receiving at least one inelastic connector (e.g., wire), and allowing that inelastic connector to move axially through the apertures 32.

Figure 5:
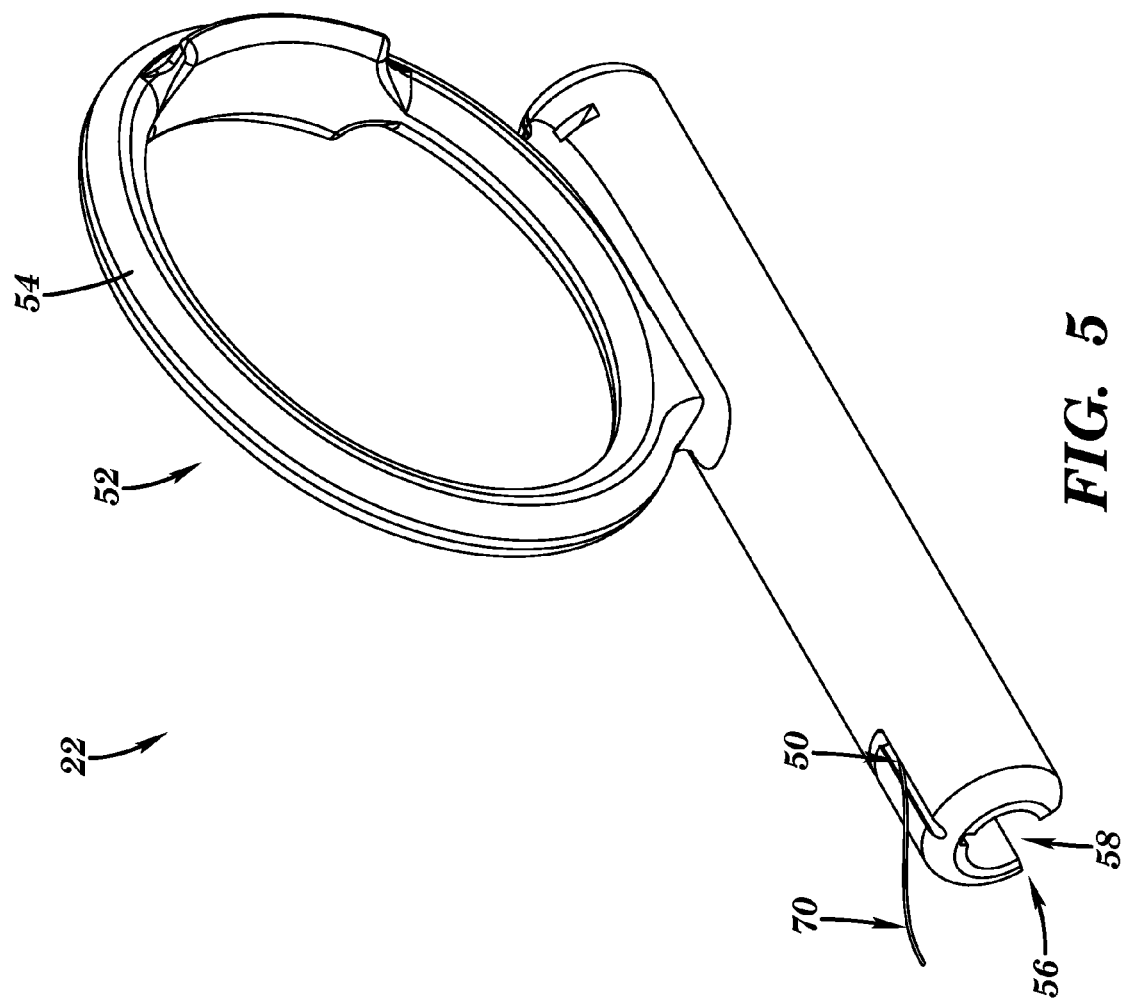
FIG. 5 shows a three-dimensional perspective view of one of the actuation members from the stylette of FIG. 1
Figure 6:
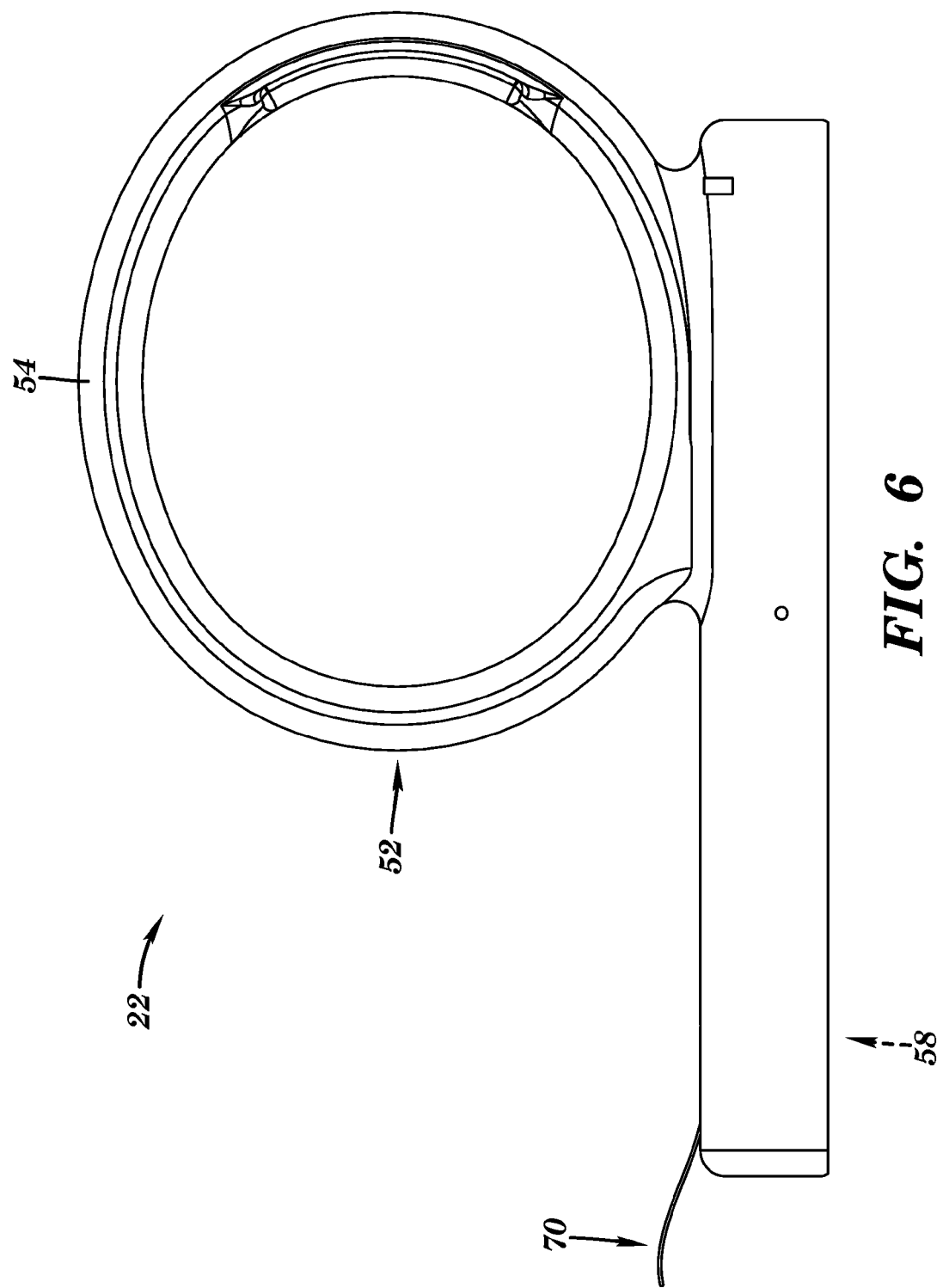
FIG. 6 shows a side view of the actuation member of FIG. 5.

FIG. 5 shows a three-dimensional perspective view of one of the actuation members 22 according to various embodiments. FIG. 6 shows a side view of the actuation member 22 of FIG. 5. As shown, the actuation member 22 can include a notch 50 for connecting the actuation member 22 with a portion of the substantially inelastic connector 70 (e.g., an end of the connector, such as a wire). The notch 50 can include a slot, opening, tab, hook, etc., for engaging the portion of the wire, and coupling that portion of the wire with the actuation member 22. The actuation member 22 shown in FIG. 5 can be substantially symmetrically aligned with another actuation member (e.g., actuation member(s) 22A, 22B in FIG. 1) about the primary axis (A) of the tube member 28. The actuation member(s) 22 can include an engagement member 52 that is sized to engage at least one finger of the operator of the stylette 2. In some cases, the engagement member 52 can include a tab, a flange, a ridge, or any other member sized to engage at least one human finger. As shown, in some embodiments, the engagement member 52 includes a loop 54 (also called a finger loop) that is sized to engage at least one human finger. In some embodiments, the loop 54 can be a substantially complete circular loop, however, in other cases, the loop 54 could be a semi-circular member. Where the loop 54 is a substantially circular loop (as shown in FIG. 5), in some examples, the loop 54 can have a radius of approximately 0.35 inches to approximately 0.85 inches. The actuation member 22 can further include a slot 56 extending along its primary axis (a) for engaging one of the guide members 24 (FIG. 1). As described herein, the slot 56 can be sized to fit the guide member 24 and remain coupled with the guide member 24 during movement of the actuation member 22. That is, the inner diameter of the slot 56 can be only nominally larger than the outer diameter of the guide member 24. The slot 56 includes a narrowed opening 58 on the bottom side (opposing the loop 54) of the actuation member 22, where the narrowed opening 58 is smaller than the inner diameter of the slot 56 and the outer diameter of the guide member 24. This allows the actuation member 22 to stay coupled with the guide member 24 during operation of the stylette 2.

Figure 7B:
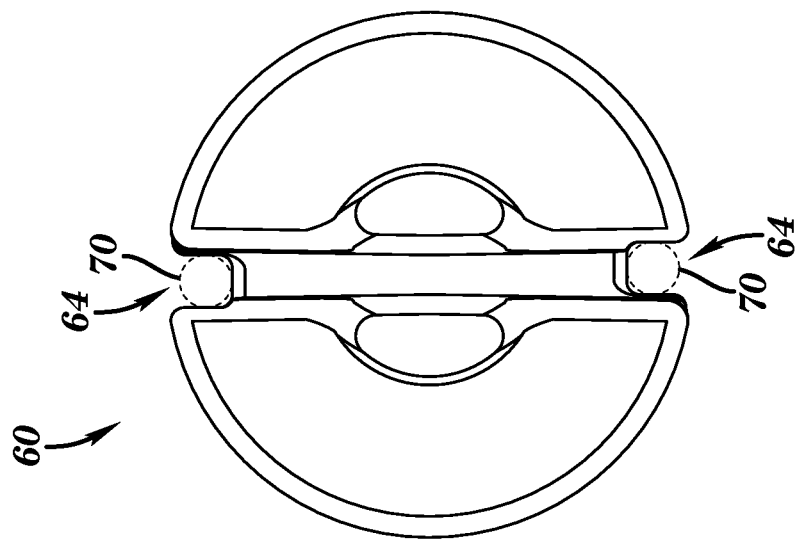
FIG. 7B shows an end view of the end cap from FIG. 7A.
Figure 7A:
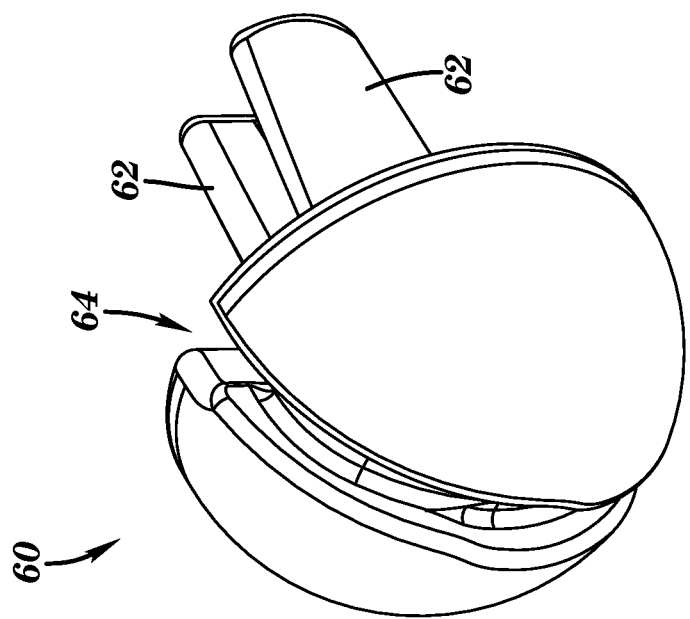
FIG. 7A shows a three dimensional perspective view of an end cap from the stylette of FIG. 1 according to various embodiments.

FIGS. 7A and 7B show a three-dimensional perspective view, and an end view, respectively, of the end cap 60 of the tip 36 (FIG. 1). As shown, the end cap 60 can include couplers 62 for engaging the distal end of the tube 28 (at the tip 36 of the semi-rigid section 32). These couplers 62 can be tapered to fix the end cap 60 within the inner diameter of the distal end of the tube 28. Also shown, the end cap 60 can include slots 64 for retaining the distal end of the substantially inelastic connector 70, shown in phantom in FIG. 7B, coupling the end cap 60 with the actuation members 22. As shown, the end cap 60 can include two slots 64 for retaining the distal end of two distinct substantially inelastic connectors 70. By retaining the inelastic connectors 70, the end cap 60 can be pulled in one of two directions at a given time, based upon which actuation member 22A, 22B is actuated at the control member 20. It is understood that the end cap 60 could include any number of slots 64 for engaging any number of substantially inelastic connectors 70. That is, in some cases, the end cap 60 could include 3, 4, or more slots for engaging a corresponding number of inelastic connectors 70. In these cases, the tip 36 of the stylette 2 can be designed to move in more than two directions from its rest position, and the end cap 60 can facilitate such movement in response to actuation at the control member 20.

Various embodiments of the invention include methods of using a stylette, e.g., the stylette 2 shown and described with reference to FIG. 1. In some cases, the method can include:

Process P1: inserting an intubating stylette (e.g., intubating stylette 2, FIG. 1) into a throat region of a patient (e.g., a human patient);

Process P2: actuating an actuation member of the intubating stylette to initiate movement of the tip of the tube member between a first position and a second position while the intubating stylette is within the throat region of the patient; and Process P3 (potential additional process): de-actuating the actuation member to return the tip of the tube member from the second position to the first position.

In some cases, where the stylette (e.g., stylette 2) includes two actuation members, and the actuation member is movable between at least three distinct positions, a method can include:

Process P11: actuating a first one of the two actuation members to move the tip of the stylette tube member between a first position and a second position while the intubating stylette is within the throat region of the patient;

Process P12: de-actuating the first one of the two actuation members to move the tip of the tube member between the second position and the first position while the intubating stylette is within the throat region of the patient;

Process P13: subsequently actuating a second one of the two actuation members to move the tip of the tube member between the first position and a third position while the intubating stylette is within the throat region of the patient.

It is understood that in various embodiments described herein, actuation of the actuation member(s) 22 (FIG. 1) can initiate a corresponding, substantially linear response in the tip 36. That is, movement of the actuation member 22 a distance of x from its resting position can cause the tip 36 to move approximately a distance x from its rest position (I) (e.g., toward another position (II), (III), etc.).

In various embodiments, components described as being "coupled" to one another can be joined along one or more interfaces. In some embodiments, these interfaces can include junctions between distinct components, and in other cases, these interfaces can include a solidly and/or integrally formed interconnection. That is, in some cases, components that are "coupled" to one another can be simultaneously formed to define a single continuous member. However, in other embodiments, these coupled components can be formed as separate members and be subsequently joined through known processes (e.g., fastening, ultrasonic welding, bonding).

The terminology used herein is for the purpose of describing particular example embodiments only and is not intended to be limiting. As used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on", "engaged to", "connected to" or "coupled to" another element or layer, it may be directly on, engaged, connected or coupled to the other element or layer, or intervening elements or layers may be present. In contrast, when an element is referred to as being "directly on," "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Spatially relative terms, such as "inner," "outer," "beneath", "below", "lower", "above", "upper" and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to an individual in the art are included within the scope of the invention as defined by the accompanying claims.

I claim:

1. An intubating stylette, comprising:
   a handle member having a base and a handle tip extending from the base, the handle member adapted for engaging a hand of an operator;
   a control member coupled to the tip of the handle member, the control member including at least one actuation member sized and adapted to engage with a finger from the hand of the operator;
   a tube member coupled to the control member, the tube member including a tip that is movable between at least two positions when the at least one actuation member is moved from a first position to a second position,
   two substantially inelastic connectors extending from the control member to the tip of the tube member, the two substantially inelastic connectors coupled with the at least one actuation member,
   wherein the at least one actuation member includes a set of two actuation members each connected with one of the two substantially inelastic connectors at a first end of the corresponding substantially inelastic connector,
   wherein the control member includes a set of two actuation member guides, each actuation member guide adapted for guiding each actuation member between the first position and the second position,
   wherein each actuation member in the set of two actuation members moves independently of the other actuation member along the respective actuation member guide.

2. The intubating stylette of claim 1, wherein the tube member includes:
   a substantially rigid substantially straight section directly coupled to the control member; and
   a substantially rigid substantially arced section directly coupled to the substantially rigid substantially straight section at a distal end of the substantially rigid substantially straight section.

3. The intubating stylette of claim 2, wherein the tip of the tube member that is movable between the at least two positions is coupled to an end of the substantially rigid substantially arced section.

4. The intubating stylette of claim 3, wherein the at least two positions include at least three positions including:
   a rest position;
   a positive displacement position; and
   a negative displacement position.

5. The intubating stylette of claim 4, wherein the positive displacement position is approximately one degree to approximately 90 degrees from the rest position as measured in a first direction from a reference axis, and wherein the negative displacement position is approximately one degree to approximately 90 degrees from the rest position as measured in a second direction from the reference axis, the second direction opposing the first direction.

6. The intubating stylette of claim 1, wherein the set of two actuation members are substantially symmetrically aligned about a primary axis of the tube member.

7. The intubating stylette of claim 6, wherein each actuation member in the set of two actuation members includes a notch for retaining a portion of the at least one substantially inelastic connector.

8. The intubating stylette of claim 1, wherein the movement of the actuation member from the first position to the second position is substantially linearly correlated with the movement of the tip of the tube member between the at least two positions.

9. The intubating stylette of claim 1, further comprising a tapered retainer member connecting the control member and the tube member.

10. The intubating stylette of claim 9, further comprising:
    at least one wire extending from the control member to the tip of the tube member, the at least one wire coupled with the at least one actuation member,
    wherein the tapered retainer member includes at least one slot extending therethrough sized to receive the at least one wire.

11. The intubating stylette of claim 1, wherein the base of the handle member includes at least one contour and at least one recess adapted to engage the hand of the operator.

12. The intubating stylette of claim 11, wherein the at least one contour includes one contour and the at least one recess includes two recesses, wherein the one contour is located between the two recesses.

13. The intubating stylette of claim 1, further comprising a cap engaged with the tip of the tube member, the cap having two slots, each of the two slots retaining a second end of each of the two substantially inelastic connectors, the second end opposing the first end of each of the two substantially inelastic connectors.

14. A method, performed by an operator, the method comprising:
    inserting an intubating stylette into a throat region of a patient, the intubating stylette having:
      a handle member with a base and a handle tip extending from the base, the handle member adapted for engaging a hand of the operator;
      a control member coupled to the tip of the handle member, the control member including at least one actuation member sized and adapted to engage with a finger from the hand of the operator; and
      a tube member coupled to the control member, the tube member including a tip that is movable between at least two positions when the at least one actuation member is moved from a first position to a second position;
      two substantially inelastic connectors extending from the control member to the tip of the tube member, the two substantially inelastic connectors coupled with the at least one actuation member,
      wherein the at least one actuation member includes a set of two actuation members each connected with one of the two substantially inelastic connectors at a first end of the corresponding substantially inelastic connector, wherein the control member includes a set of two actuation member guides, each actuation member guide adapted for guiding each actuation member between the first position and the second position, wherein each actuation member in the set of two actuation members moves independently of the other actuation member along the respective actuation member guide; and actuating the at least one actuation member to initiate movement of the tip of the tube member between the first position and the second position while the intubating stylette is within the throat region of the patient.

15. The method of claim 14, further comprising de-actuating the at least one actuation member to return the tip of the tube member from the second position to the first position.

16. The method of claim 14, wherein the tip of the tube member is further movable between the first position, the second position, and a third position opposite the second position, the method further including:

actuating a first one of the two actuation members to move the tip of the tube member between the first position and the second position while the intubating stylette is within the throat region of the patient;

de-actuating the first one of the two actuation members to move the tip of the tube member between the second position and the first position while the intubating stylette is within the throat region of the patient; and subsequently actuating a second one of the two actuation members to move the tip of the tube member between the first position and the third position while the intubating stylette is within the throat region of the patient.

17. An intubating stylette, comprising:

a handle member for engaging a hand of an operator;

a control member coupled to the handle member, the control member including at least one actuation member sized to engage with a finger from the hand of the operator; and a tube member coupled to the control member, the tube member including a tip that is movable across a range of positions in response to the at least one actuation member being moved across a corresponding range of positions;

at least one substantially inelastic connector extending from the control member to the tip of the tube member, the at least one substantially inelastic connector coupled with the at least one actuation member, wherein the at least one actuation member includes a set of two actuation members each connected with an end of the at least one substantially inelastic connector, wherein the control member includes a set of two actuation member guides, each actuation member guide adapted for guiding each actuation member between the first position and the second position, wherein each actuation member in the set of two actuation members moves independently of the other actuation member along the respective actuation member guide.

18. The intubating stylette of claim 17, further comprising:

a tapered retainer member connecting the control member and the tube member;

at least one substantially inelastic connector extending from the control member to the tip of the tube member, the at least one substantially inelastic connector coupled with the at least one actuation member, wherein the tapered retainer member includes at least one slot extending therethrough sized to receive the at least one substantially inelastic connector.

19. The intubating stylette of claim 18, wherein the at least one substantially inelastic connector includes a wire.

20. The intubating stylette of claim 18, wherein the actuation member includes a notch for retaining a portion of the at least one substantially inelastic connector.

* * * * *